(12) United States Patent  
Kent et al.

(10) Patent No.: US 7,563,244 B2
(45) Date of Patent: Jul. 21, 2009

(54) DEVICE FOR MIXING AND DELIVERING PHARMACEUTICAL COMPOSITIONS

(75) Inventors: Blair M Kent, Camas, WA (US); Clement C Lo, Oswego, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 712 days.

(21) Appl. No.: 10/285,827

(22) Filed: Oct. 31, 2002

(65) Prior Publication Data

US 2004/0084555 A1 May 6, 2004

(51) Int. Cl.
 *A61M 37/00* (2006.01)
(52) U.S. Cl. .......................................... 604/82; 604/48
(58) Field of Classification Search .................. 604/82, 604/85, 503, 518, 185; 222/214; 347/5; 128/200.14, 200.23, 200.21
 See application file for complete search history.

(56) References Cited

U.S. PATENT DOCUMENTS

| 3,895,631 | A |  | 7/1975 | Buckles et al. |
| 3,934,585 | A |  | 1/1976 | Maurice |
| 4,265,241 | A |  | 5/1981 | Portner et al. |
| 4,336,800 | A |  | 6/1982 | Pastrone |
| 4,913,699 | A |  | 4/1990 | Parsons |
| 5,061,243 | A |  | 10/1991 | Winchell et al. |
| 5,241,954 | A | * | 9/1993 | Glenn ............... 128/200.18 |
| 5,368,582 | A |  | 11/1994 | Bertera |
| 5,474,059 | A |  | 12/1995 | Cooper |
| 5,743,252 | A |  | 4/1998 | Rubsamen et al. |
| 5,881,716 | A | * | 3/1999 | Wirch et al. ........... 128/200.16 |
| 5,894,841 | A | * | 4/1999 | Voges ................. 128/203.12 |
| 5,925,011 | A | * | 7/1999 | Faict et al. ................ 604/29 |
| 5,951,531 | A | * | 9/1999 | Ferdman et al. ............. 604/290 |
| 6,010,492 | A |  | 1/2000 | Jacobsen et al. |
| 6,126,642 | A |  | 10/2000 | Kriesel et al. |
| 6,210,361 | B1 |  | 4/2001 | Kamen et al. |
| 6,237,589 | B1 |  | 5/2001 | Denyer et al. |
| 6,325,475 | B1 |  | 12/2001 | Hayes et al. |
| 6,368,562 | B1 | * | 4/2002 | Yao .......................... 422/100 |
| 6,406,121 | B1 | * | 6/2002 | Benjamin et al. ............ 347/20 |
| 2002/0117517 | A1 | * | 8/2002 | Unger et al. ................ 222/214 |
| 2003/0065294 | A1 | * | 4/2003 | Pickup et al. ............... 604/304 |

FOREIGN PATENT DOCUMENTS

WO  WO 9930832 A1 * 6/1999

\* cited by examiner

*Primary Examiner*—Laura A Bouchelle (57) ABSTRACT

A device and method for delivering a pharmaceutical composition. The device includes an electronically controllable jetting device in communication with a source

FIG. 1

- EJECT PHARMACOLOGICALLY ACTIVE FLUID ONTO MIXING MEDIUM — 10
- DIRECT FLUID FROM MIXING MEDIUM TO END-USE DESTINATION — 20

FIG. 2

- 50 — EJECT PHARMACOLOGICALLY ACTIVE FLUID ONTO MIXING SURFACE
- 60 — EJECT PROPORTIONATE AMOUNT OF COMPATIBLE FLUID ONTO MIXING SURFACE
- 70 — RETAIN EJECTED FLUIDS FOR INTERVAL SUFFICIENT TO MIX
- 80 — ATOMIZE MIXED FLUIDS
- 90 — DIRECT ATOMIZED FLUIDS TO END-USE DESTINATION

DEVICE FOR MIXING AND DELIVERING PHARMACEUTICAL COMPOSITIONS

FIELD OF THE INVENTION

The present invention is directed to a method and device for delivering a pharmacologically active fluid or fluids into a mixing medium.

BACKGROUND OF THE INVENTION

Various devices have been suggested for dispensing precisely controlled quantities or ratios of a pharmacologically active fluid or fluids into a carrier stream for delivery to an end use destination such as a patient. Heretofore, it has been difficult to precisely regulate quantity and/or ratio of various pharmacologically active fluids being dispensed. Additionally, precise and effective mixture of multiple materials has been problematic.

SUMMARY OF THE INVENTION

Disclosed herein is a device for dispensing pharmaceutical compositions which include an electronically controllable jetting device in communication with a source of a pharmacologically active material and a solid or fluidic mixing medium for receiving the ejected pharmacologically active material and directing it toward an end use destination.

DETAILED DESCRIPTION OF EMBODIMENTS

Figure 1:
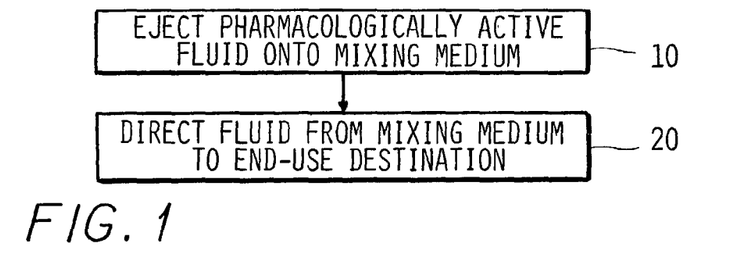
FIG. 1 is a process diagram of a method for delivering a pharmaceutical composition.

As depicted in FIG. 1, disclosed is a method for delivering a pharmaceutical composition which includes the steps of ejecting at least one pharmacologically active fluid from an electronically controllable jetting device toward a mixing medium 10. The ejected fluid is then directed from the mixing medium toward an end-use destination at 20.

As used herein, the term "pharmaceutical composition" is defined as a material having physiological effect on the person to whom it is administered. Pharmaceutical compositions can include, but are not limited to, materials which are regulated by governmental agencies such as the United States Food and Drug Administration. Thus, pharmaceutical compositions as used herein include prescription drugs, as well as materials suitable for distribution as non-prescription drugs. Also included are materials which are not regulated but are commonly classified as nutraceuticals or are generally recognized as being safe and effective for their intended end use. As used herein, "pharmaceutical composition" can refer to a blend or material containing two or more suitable compounds or a suitable compound in a carrier medium.

It is contemplated that at least one of the compounds employed in the pharmaceutical composition will be a pharmacologically active fluid. Additional compounds may also have pharmacological activity or may be recognized as materials which complement the primary pharmacologically active fluid or interact with the primary pharmacologically active fluid in a manner which is advantageous to the uptake, use or other action of the primary fluid. Thus, additional materials present in the pharmaceutical composition prepared may be ones which are not typically recognized as having pharmacological activity in and of themselves.

The term "pharmacologically active" is employed herein to include materials having pharmacological or psychopharmacological activity, i.e., a known, suspected or accepted dose effect or cumulative effect on the individual to whom they are administered. Such materials can include, but are not limited to prescription drugs, non-prescription drugs and the like. The secondary material may have pharmacological activity which is of a similar or different class than the first or primary pharmacologically active material. For example, one pharmacologically active material may have analgesic effects while a second may be classed as an antibiotic. Thus, the method disclosed herein contemplates the admixture of various different pharmacologically active fluids provided that the materials can be brought into contact with one another in the mixing medium in a safe and effective manner. The materials which are mixed can include materials which are introduced for non-medicinal purposes such as materials which aid in mixture, transport, and the like. It is also contemplated that materials in the pharmaceutical composition can include compounds or materials which, when administered in the presence of a pharmacologically active fluid, either activate or promote the desired activity of the pharmacologically active fluid upon administration or are useful in addressing or mitigating various side effects which may arise with the administration of the pharmacologically active fluid. By way of non-limiting example, it is contemplated that a pharmaceutical composition may include a suitably pharmacologically active drug or drugs as well as one(s) which may address side effects such as nausea, dizziness or the like, provided that the two or more materials having an acceptable interaction panel can be brought together in the mixing medium.

The term "fluid" as used herein is defined as a material capable of ejection from an electronically controllable jetting device. As used herein, the term "fluid" encompasses materials traditionally referred to as liquids as well as compounds or materials which are fluidizable solids.

The term "electronically controllable jetting device" as used herein is taken to include various microfluidic pump devices which eject quantities of a given material upon receipt of a suitable electronic command. Examples of devices having suitable structure and architecture include devices typically referred to as ink jets. Such ink jets typically include ejection nozzles or orifices which are electronically actuatable. These devices can include devices which are generally referred to as thermal jetting devices, piezoelectric jetting devices and the like.

The term "mixing medium" includes solid and/or fluidic surfaces onto which material ejected from an electronically controllable jetting device can be directed. Solid media include materials which generally provide a solid, non-absorptive surface onto which the ejected materials can be introduced. The surface is one which can initiate a mixing event whereby the ejected pharmacologically active fluid or fluids and any auxiliary materials can begin to blend. It is also contemplated that solid materials can include materials which exhibit a degree of classic porosity which will facilitate or permit the movement of portions of the ejected pharmacologically active fluid(s) through pores defined therein. Such materials can include appropriate wire mesh, porous membrane or the like. The mixing medium can also include fluid or fluidic materials such as liquids which have a defined surface and permit the dispersive impingement of ejected pharmacologically active fluids into the fluidic material.

The term "end use destination" as used herein can include, but is not limited to, individuals for whom the pharmaceutical composition has been prescribed. The end use destination as defined herein can also include various holding tanks, reservoirs and the like which are intermediate to the individual for whom the pharmaceutical composition is prescribed.

It is contemplated that the method disclosed herein can have utility in both human and non-human application processes. Thus, it is contemplated that the method and associated device can be used in various medical, veterinary, zoological and botanical applications. Thus, while the method and associated device are described in terms of medical applications, this is to be construed as exemplary and not limitative of the scope or nature of the device disclosed herein.

In the method for delivering a pharmaceutical composition, at least one pharmacologically active fluid is ejected from an electronically controlled jetting device toward a mixing medium as outlined at reference numeral 10 in FIG. 1. The ejection event of the method disclosed herein can involve the dispensing of defined quantities of material(s) from at least one electronically controllable jetting device toward a mixing medium. It is contemplated that the electronically controllable jetting device will be positioned a discrete distance from the surface of the mixing medium such that direct physical contact between the electronically controlled jetting device and the mixing medium is minimized or prevented. The ejection event typically contemplated herein involves the movement of discrete quantities of the pharmacologically active fluid(s) and any auxiliary materials from a suitable electronically controllable jetting device through space to the surface of the desired mixing medium.

The discrete quantities of pharmacologically active fluid(s) and auxiliary materials are introduced to the mixing medium where the mixing event commences. The method disclosed herein contemplates that degrees of the mixing event begin when the materials come into contact with the mixing medium. A degree of premixing can occur in certain circumstances as the materials are ejected from the electronically controllable jetting devices. However, it is contemplated that the major portion of the mixing event whereby various materials which will be contained in the resulting pharmaceutical composition are brought into contact and mix occurs upon contact with the mixing medium. It is to be understood that the mixing event can continue as the materials are directed from the mixing medium toward the end use destination.

The defined quantities of various fluid(s) ejected from associated electronically controllable jetting devices can be dispensed as measured quantities. Thus, the method contemplates that precise amount of various materials can be ejected to provide a pharmaceutical composition of the potency and dosage required. It is also contemplated that the method disclosed herein can be used to provide pharmaceutical compositions having precise ratios of various materials which can be delivered or administered on a continuous basis depending upon the nature of the pharmaceutical composition and its desired use or effect. For example, a specific dose of a material based upon the requirements of the patient can be administered. As such, dosage situations can include but are not limited to administration of antibiotics, chemotherapeutic agents, and other materials having either dose toxicity, dose maximums, or the like. In other circumstances, the materials administered may be ones which require administration of precise ratios but can be administered on a continuous or semi-continuous basis. Such materials may include pulmonary absorption anesthetics, topical application materials, breathing treatments and the like. The electronically controllable jetting devices can be utilized to provide either precise ratio, measured dose or combinations thereof.

In the method of the present invention, a control limitation can be exerted on the jetting device such that the pharmacologically active fluid(s) and/or any auxiliary fluids are ejected from the jetting device(s) at a rate defined by a control limitation. The control limitation can include, but is not limited to, preset definitions regarding maximum dosage, permissible administration rate, preferred or desired ratios of various materials, and the like. It is also contemplated that control limitations can include additional operating parameters which govern the function and actuation of the various electronically controlled jetting devices.

It is contemplated that the method of the present invention can be utilized to achieve ejection of various materials from a plurality of electronically controllable jetting devices fluidically coupled to a plurality of storage receptacles. Each storage receptacle can be configured to contain a suitable fluid. The plurality of storage receptacles and associated electronically controllable jetting devices can achieve ejection of a variety of pharmacologically active fluid(s) according to an appropriate ejection protocol. Additionally, it is contemplated that the plurality of storage receptacles and associated electronically controllable jetting devices can be utilized to eject at least one fluid which is pharmacologically active and at least one auxiliary fluid compatible with the pharmacologically active material. The storage receptacles can be positioned either remote or proximate to the associated electronically controllable jetting devices. Thus, delivery of the stored fluids can be accomplished either by off-axis or on-axis modalities. It is also contemplated that the delivery of appropriate fluids for ejection through the associated electronically controllable jetting devices can be accomplished by a combination of off-axis and on-axis modalities depending upon the circumstances presented.

The disclosed method also contemplates the step of introducing a carrier stream proximate to the mixing medium. The carrier stream is one which includes or is composed of a material compatible with the pharmacologically active material(s) ejected from the jetting device. The carrier stream can be any fluid material such as a liquid or a gas which is capable of being introduced from an appropriate source and of conveying the ejected fluids from the mixing medium toward the end use destination. For example, in situations where it is desired that the pharmaceutical composition be delivered for pulmonary uptake, a suitable gaseous carrier stream can be employed. The gaseous carrier stream will be conveyed in a manner which will permit the eventual atomization of the ejected fluids subsequent to the mixing medium. Examples of such gases include compressed air, oxygen and other materials suitable for pulmonary uptake. Alternately, the carrier stream may be a liquid suitable for ingestion or infusion.

Ejection of pharmacologically active material from the electronically controllable jetting device can be governed by at least one conditional input. Suitable conditional inputs can be those which will have a direct or indirect effect on the need for the pharmacologically active component of the pharmaceutical composition, the uptake of the material, its metabolic decomposition by the user and the like. Thus, the conditional input can include at least one of user health, current external environmental conditions, general activity level, and metabolic condition. User health can include any of a number of decisional parameters which medical personnel would employ or consider in determining the administration, dosage and use of a suitable pharmacologically active material. These can include, for example, factors such as user blood pressure, cardiac condition, respiration condition, immunological condition and the like. Metabolic conditions are considered to be those which effect the utilization of a given pharmacologically active material. These can include, but are not limited to, cellular uptake and/or rate of metabolization of a pharmacologically active material. Other examples of metabolic condition can include particular circumstances regarding clearance of the administered material from the biological system. Such factors can include, but are not limited to, liver function, renal function, pulmonary function, and the like. Additionally, metabolic condition is taken to include other factors related to the utilization of various materials by the individual. Such metabolic conditions can include the presence or absence of diabetes, phenylketonuria, and the like.

It is also possible that conditional input can be based upon a qualitative analysis of general activity level. Thus, individuals engaged in strenuous physical activity or contemplated such strenuous physical activity, can result in a conditional input which adjusts the rate or quantity of pharmacologically active fluid ejected by the electronically controllable jetting device. One such non-limiting example would pertain to the administration of various fast-acting asthma drugs in an asthmatic individual. Where increased respiration or demands upon the pulmonary system are anticipated or encountered, the rate or quantity of material could be increased to compensate for increased demands engendered by an increase in general activity level. External environmental conditions which can be incorporated into conditional input can include, but are not limited to, various weather factors such as temperature, levels of smog or particulate material in the air, and the like.

As indicated previously, the mixing medium can be either a solid, porous solid, or a fluid having a mixing surface onto which the ejected material can be delivered. Where the mixing medium is solid or porous solid, it is contemplated that the material will have a mixing surface contour configured to convey pharmacologically active fluid(s) and any auxiliary materials ejected thereon in a manner which will initiate mixing of the ejected introduced materials. The mixing surface can have an appropriate exit to permit ejected materials to be conveyed to subsequent down-stream locations and the end use destination. It is contemplated that the mixing surface can be configured to initiate mixing of the pharmacologically active fluids and auxiliary materials as well as assisting in conveying these materials to an associated atomizing nozzle.

Alternately, it is contemplated that the mixing medium can be a fluid which is compatible with the pharmacologically active fluid ejected from the electronically controlled jetting device. In such circumstances, it is contemplated that the fluid mixing medium and ejected pharmacologically active material will be conveyed together to subsequent down-stream location and, ultimately, to the end use destination as desired or required. Examples of fluids compatible with the pharmacologically active fluid ejected from the electronically controlled jetting device include but are not limited to various pharmaceutical grade materials such as saline solutions, dextrose solutions, and the like. Where a fluid mixing medium is employed, it is theorized that ejection of the pharmacologically active fluid into contact with the fluid mixing medium by means of electronically controllable jetting devices initiates and facilitates the mixing dispersal of the various ejected material or materials within the fluid mixing medium permitting suitable blending of the various ejected material(s).

It is also contemplated that the mixing medium can be a combination of a solid and liquid surface. One such hybrid mixing medium would include a fluid material having an overlying solid mesh surface onto which the ejected pharmacologically active fluids are introduced. It is contemplated that such mesh surface would permit the transfer of the ejected fluids into the communicating fluid mixing media. The mesh could be employed to facilitate mixing or dispersal of the ejected materials. Suitable meshes would include materials having a screen or pore size suitable for permitting the transfer of the ejected material(s) into the communicating fluid portion. Such materials can include wire mesh, porous membrane and the like.

Figure 2:
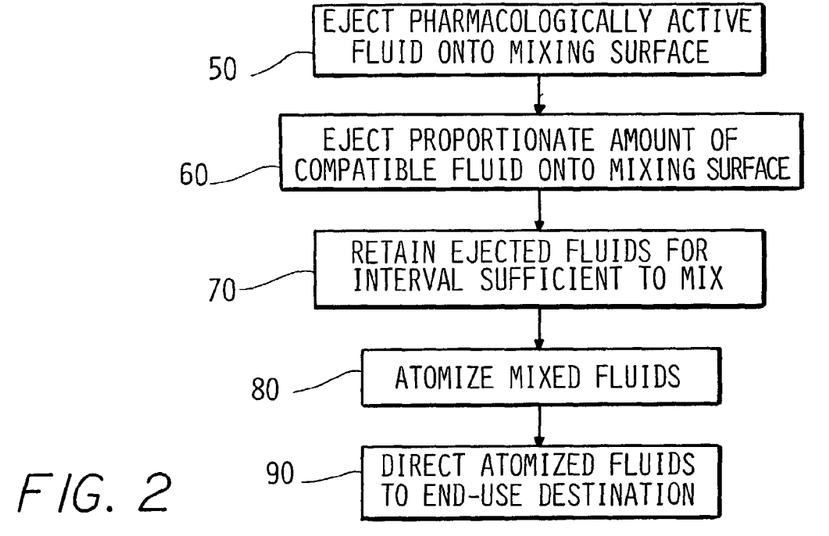
FIG. 2 is a process diagram of an embodiment of a method for delivering a pharmaceutical composition.

Referring now to FIG. 2, a method for delivering a pharmaceutical composition having multiple materials in proportionate amounts as outlined. In the method disclosed, quantities of fluid materials are ejected from associated electronically controllable jetting devices onto a mixing surface at reference numeral 50. Of the fluid materials ejected, at least one fluid material exhibits pharmacological activity.

Proportional amounts of a compatible fluid can be ejected together with the fluid material having pharmacological activity as at reference numeral 60. The nature of the second fluid can be one which exhibits pharmacological activity or is otherwise suitable for use in combination with a material having pharmacological activity to provide complementary or combinational effects. Thus, it is contemplated a compatible fluid material can be one which exhibits a pharmacological response different from the first material or one which synergistically acts with the first material to enhance or augment that activity or facilitate uptake. It is also contemplated that the material may be one which palliates or mitigates undesirable side effects or one which facilitates blending or compounding of various other components.

The ejected fluids are retained on the mixing surface for an interval sufficient to permit the initiation of blending or mixing of the ejected materials as at reference numeral 70. After contact of the fluid materials on the mixing surface, the ejected fluids can be removed from the mixing surface toward a suitable atomizing device to atomize the mixed fluids as at reference numeral 80. It is to be understood that retention of the ejected fluids on the mixing surface can be very brief or prolonged as desired to achieve appropriate mixing. It is further to be understood that the mixing event can be initiated on the mixing surface and can proceed for any interval subsequent to the exit of the ejected fluids from the mixing surface to down-stream points prior to atomization. The retention interval is that sufficient to permit the occurrence of suitable mixing by the time the materials reach the atomization point and ultimately the end use destination. Thus, thorough mixture while the ejected materials are resident on the mixing surface may occur in certain circumstances. However, simple initiation of the mixing event is also considered within the purview of the method as disclosed. Thus, at minimum, the ejected fluid materials contact the mixing surface in a manner which initiates the mixing event and are then removed from the mixing surface into appropriate downstream devices for conveyance to an appropriate atomizing device such as an atomizing nozzle which is configured to atomize the mixed fluids in a manner suitable for further conveyance to down-stream locations and/or ultimately to the end use destination.

The ejected fluids are directed toward an end-use destination upon exit from the atomizing nozzle, as at reference numeral 90.

The proportionate quantities of the fluid materials can be ejected at programmably variable rates which can be controlled by suitable control devices exerting appropriate control commands on the associated electronically controllable jetting devices. The programmably variable rates are determined, at least in part, by at least one conditional input electronically receivable by the jetting device. These inputs can include, but are not limited to, at least one of user heath, current environmental conditions, general activity level, and metabolic condition of the intended user as these terms were outlined previously.

The method contemplates the step of introducing a carrier stream into a region proximate to an outlet of the atomizing device associated with the mixing surface. The carrier stream can be one which will assist in directing and/or conveying the material which exits the atomizing device onto the end use destination. Such carrier stream materials typically will be those compatible with the pharmacologically active fluid material or materials ejected from an associated electronically controllable jetting device. Typically, where multiple fluids are ejected, it is contemplated that the carrier stream is composed of a turbulent material such as an atomizing gas which will facilitate the atomization of the ejected materials upon exit from the atomizing device. Suitable gases are generally those which are appropriate for use and uptake by humans or other organisms. These gases can include other entrained materials such as water vapor and the like if necessary or desired. Additionally, it is contemplated that suitable gases may include or be composed of materials which have medicinal or pharmacological effects such as anesthetics or the like.

The materials which are administered may be present in a suitable reservoir or holding tank in a pre-measured volume which defines a dosage or other desired amount(s) of material appropriate for administration. In the method disclosed, this measured volume may be ejected from the electronically controllable jetting devices in measured amounts over an appropriate time interval. Thus, with quick acting and rapid excreting materials, it is contemplated that precise proportions of materials can be administered at an appropriate rate for their delivery and uptake. In such scenarios, the proportionality of the materials is precisely regulated by the electronically controllable jetting devices while the rate of delivery includes functionality contributed by the rate of passage of the carrier stream. It is also contemplated that the proportion of materials and/or rate of delivery can be electronically variable based upon appropriate inputs. These inputs can include, but are not limited to, the conditional inputs earlier enumerated here. Thus, the method disclosed contemplates the regulation and variation of proportion and/or rate of delivery based upon appropriate external inputs which may include various biofeedback mechanisms, environmental monitoring mechanisms, and qualitative user or physician input mechanisms.

It is also contemplated that the fluid materials can be ejected from associated electronically controllable jetting devices in measured amounts or dosages. The measurement of the amount or dosage can be calculated from suitable regulation of drop volume of the materials ejected from the various electronically controllable jetting devices.

Also disclosed is a device 100 for delivering a pharmaceutical composition. The device 100 can include electronically jetting devices 112, 114 in communication with a source or sources of pharmacologically active material and/or auxiliary material compatible with the pharmacologically active material 116, 118. While the device schematically depicted in FIG. 3 illustrates two electronically controllable jetting devices and associated sources of pharmacologically active material and/or auxiliary compatible material(s), it is contemplated that the device can include multiple jetting devices associated to a variety of material(s) required to formulate the desired pharmaceutical composition. The types and nature of the pharmacologically active materials and auxiliary compatible materials which can be conveyed through the jetting device to produce the desired pharmaceutical composition can be of the nature and type discussed previously.

The pharmaceutical composition device 100 also includes a mixing device 120 positioned to receive the pharmacologically active material(s) and any auxiliary compatible materials ejected from the associated electronically controllable jetting device(s). As depicted schematically in FIG. 3, the mixing device can have a mixing surface 122 in communication with a suitable exit orifice 124. The exit orifice 124 is configured to convey the pharmaceutically active material(s) and any auxiliary compatible material(s) away from the mixing surface 122. The ejected or jetted material(s) can be conveyed away from the mixing surface by any suitable mechanism, device, or structure. As illustrated in FIG. 3, the carrier stream can be introduced through a suitable conduit member 131 from a carrier stream supply source 130. The carrier stream can proceed through conduit member 131 in the direction of arrow A to produce an appropriate atomizing effect and draw the ejected materials through exit orifice 124 into conduit 131 toward a suitable end use destination. The carrier stream is supplied in a manner suitable to provide a carrier rate sufficient to convey the pharmaceutically active material(s) and any compatible auxiliary materials to the end use destination or other intermediate destinations located downstream.

The pharmaceutical composition delivery device 100 can also include a retention reservoir located prior to exit orifice 124. The retention reservoir is configured to contain material upon exit from the electronically controllable jetting device 112, 114 until dispatch is required.

In the device as disclosed, it is contemplated that the mixing surface 122 will be configured to initiate mixing of the various materials ejected onto the mixing surface 122. The surface 122 may be smooth or contoured as desired or required to initiate and/or promote mixing. One such exemplary configuration of a solid mixing surface is presented in FIG. 4. The mixing surface 122 may include a plurality of inwardly oriented surface irregularities such as ridges 132 and troughs 134. The surface irregularities will be configured to interact with the discrete quantities of the material ejected from electronically controllable jetting devices 112,114 to initiate and/or facilitate blending and mixture of the various materials introduced onto mixing surface 122. Such mixing can be initiated upon and during contact with the mixing surface 122. The various ejected materials are drawn in a suitable fashion toward orifice 124. The materials can be introduced into a suitable carrier stream as desired or required. The configuration of mixing surface 122 is such that mixing or blending is initiated on the surface 122. It is contemplated that the turbulence and mixing action can continue upon exit from orifice 124 and conveyance toward a suitable atomizing apparatus such as that represented at reference number 128 in FIG. 7.

It is contemplated that the mixed material and carrier stream can conveyed directly to an end use destination or can be retained in a suitable holding vessel 146 prior to delivery to the end used destination in situations where this later approach would be warranted or appropriate.

Referring once again to FIG. 3, the pharmaceutical composition delivery device 100 may also include a suitable chronometric device 136 in electronic communication with jetting devices 112, 114. The chronometric device 136 is capable of measuring at least one of elapsed time and real time. It is contemplated that the chronometric device 136 can also be capable of controlling operation of the jetting device(s) based upon at least one of elapsed time and real time. Alternately, it is contemplated that the chronometric device can be placed in electronic communication with suitable control electronics 138 to permit control ejection of pharmacologically active materials and/or auxiliary compatible materials based upon at least one of elapsed time and real time.

Figure 3:
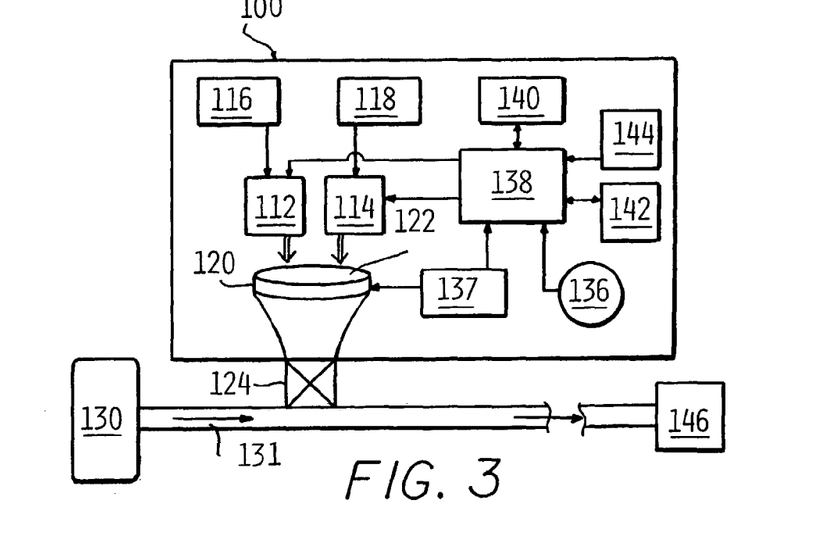
FIG. 3 is a schematic diagram of a device for delivering a pharmaceutical composition to a user.
Figure 4:
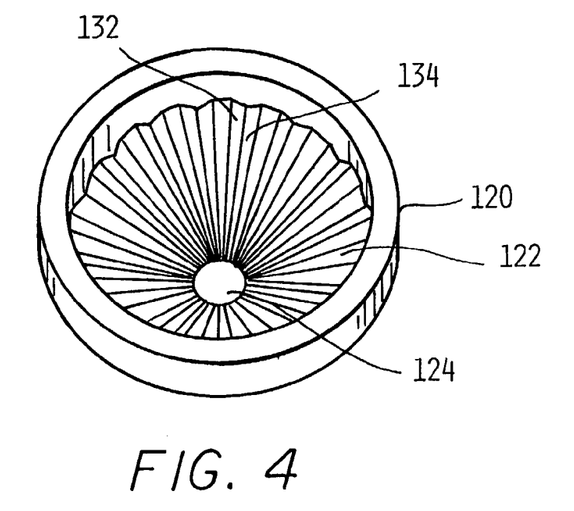
FIG. 4 is a perspective detail view of a mixing surface.

The control electronics 138 associated with the jetting device 112, 114 are configured to generate at least one command operable on the electronically controllable jetting devices. The operable command can be one which regulates or alters the volume, rate, or interval at which one or more of the pharmacologically active material(s), auxiliary compatible material(s), and the like are ejected from the jetting device into contact with the mixing surface. It is contemplated that the ejection rate, volume, dispensing interval, as well as ratios of the various dispensed materials, can be governed by various parameters which can include data regarding conditional inputs related to various elements. Such elements can include, but are not limited to, factors such as user health, external environmental conditions, physical activity level, and metabolic condition. It is contemplated that control electronics can be configured generate at least one command operable on the electronically controllable jetting devices 112, 114 based upon appropriate intermittent intervals and the like.

It is also contemplated that the control electronics 138 of the device 100 as it is disclosed can be configured to control actuation of jetting devices 112, 114 based upon the conditional input including, but not limited to, data pertaining user health, external environmental conditions, physical activity, and metabolic condition as these terms have been discussed previously. Conditional input data and programming can be contained within control electronics 138 or can be obtained through conditional input interface 140, which is in electronic communication with control electronics 138. The conditional input interface 140 can be configured to receive and process at least one input relevant in generating a command operable on the electronically controllable jetting devices 112, 114.

It is also contemplated that the device disclosed can include a data recording mechanism capable of receiving and maintaining data pertaining to at least one parameter, such as dose quantity, dose frequency, administration rate and type of material administered. The data recording mechanism can be in electronic communication with the control electronics 138 or in any suitable configuration to capture and retain information which may be relevant to individuals, health care administrators, physicians and the like.

The device as disclosed and depicted in FIG. 3 can also include a suitable user interface 144 in electronic communication with the control electronics 138. The interface 144 is capable of receiving instructions regarding at least one control parameter. It is contemplated that the control parameter may be any appropriate user-governed control element including, but not limited to, user activation, biofeedback action, and situational activation which initiate or override the function of the device 100. The device may also include suitable data recording mechanisms such as mechanism 137 capable of receiving and maintaining data pertaining to factors which can include, but are not limited to dose quantity, dose frequency, administration rate, and material composition.

The device as disclosed may be configured to be capable of interactive communication with at least one external medical source. Communication may be accomplished by medical interface 242. The medical interface 242 can permit communication with and potential modification of the dispensing protocols by medical personnel.

Connection between the reservoir 116, 118 and respective jetting devices 112, 114 can be accomplished by any suitable configuration or apparatus. It is contemplated that reservoirs 116, 118 and respective jetting devices 112, 114 can be connected by a conduit to permit off-axis delivery of materials to the jetting devices. Alternately, the reservoirs 116, 118 and respective electronically controllable jetting devices can be in direct fluidic contact with one another.

Figure 5:
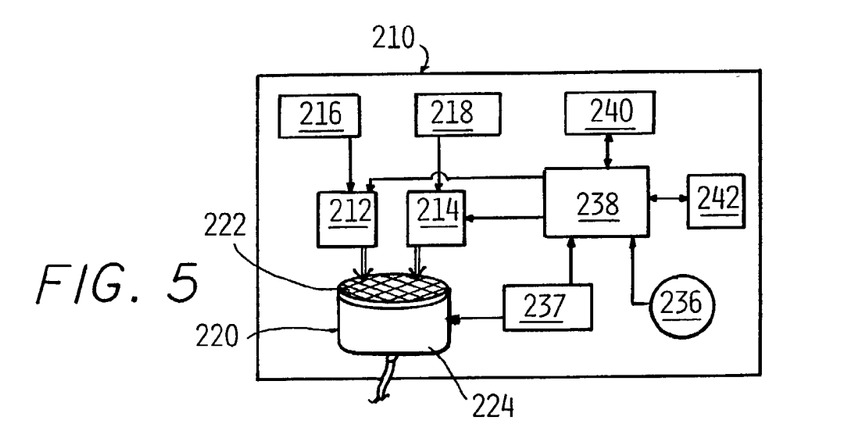
FIG. 5 is a schematic diagram of a device for delivering a pharmaceutical composition to a user.

Disclosed herein is a modified mixing dispensing device 210 for use with a medical delivery system as depicted in FIG. 5. The mixing dispensing device 210 includes electronically controllable jetting devices 212, 214 in fluid communication with at least one source of pharmaceutically active material. Such sources can include reservoirs 216, 218. The device 210 also includes control electronics 238 associated with the electronically controllable jetting devices 212, 214. The control electronics 238 includes a data storage portion 240 capable of maintaining information regarding the pharmaceutically active material conveyed through the electronically jetting devices 212, 214. The control electronics 238 may be capable of interactive communication with at least one external source. Communication can be accomplished by interface 242. It is contemplated that the external source will be capable of communicating with the medical personnel such as doctors, nurses, pharmacists and the like.

The mixing dispensing device 210 also includes a mixing medium adapted to receive the pharmaceutically active material ejected from the electronically controllable jetting devices 212, 214. The mixing medium 220 in the device 210 as disclosed can be a fluid contained in a suitable receptacle 224. The fluid can be any suitable material into which the pharmaceutically active material can be introduced and disbursed. Typical fluids are pharmaceutical grade materials suitable for ingestion, inhalation or intravenous delivery. Such materials include, but are not limited to, various saline solutions, dextrose solutions and the like.

As disclosed in FIG. 5, the mixing medium 220 can also include a suitable porous mesh or membrane 222 in fluid contact with the fluid mixing medium to further collect, mix and disperse the ejected pharmaceutically active material into the fluid mixing medium. The porous solid 222 is positioned to be in fluid communication with a contact surface of the fluid mixing material. It is contemplated that the porous solid can facilitate mixing of materials ejected from electronically controllable jetting devices 212, 214 as well as integration of these materials into the fluid mixing medium. Movement of the ejected fluids through the porous solid can be facilitated by maintaining the fluid at a slight negative pressure.

The mixing dispensing device 210 can be configured to dispense a plurality of pharmaceutically active materials in programmably variable quantities or rates. The device 210 can also be configured to dispense auxiliary compatible material in appropriate quantities and/or rates. While the device as illustrated in FIG. 5 presents two electronically controllable jetting devices 212, 214 in association with reservoirs 212, 218, it is contemplated that any number of jetting devices and reservoirs can be included as desired or required.

The mixing dispensing device 210 can also include an chronometric device 236 in electronic communication with the electronically controllable jetting device 212, 214. The chronometric device 236 can be one which is capable of controlling ejection of pharmacologically active material as well as any auxiliary complimentary materials based upon at least one of elapsed time and real time.

The device 210 can also include a data recording mechanism 237 capable of receiving and maintaining data pertaining to at least one of dose quantity, dose frequency, administration rate, and type of material administered. It is contemplated that the electronically jetting devices 212, 214 are programmably actionable based upon a conditional input which can include at least one of user health, external environmental conditions, general activity level, and metabolic condition.

Figure 6:
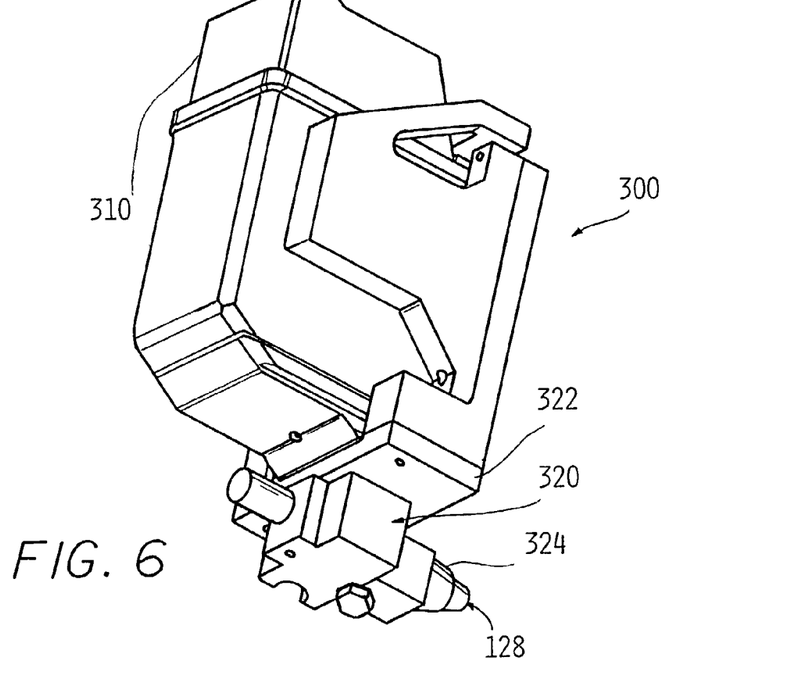
FIG. 6 is a perspective view of a cartridge for use with a medical dispensing system.
Figure 7:
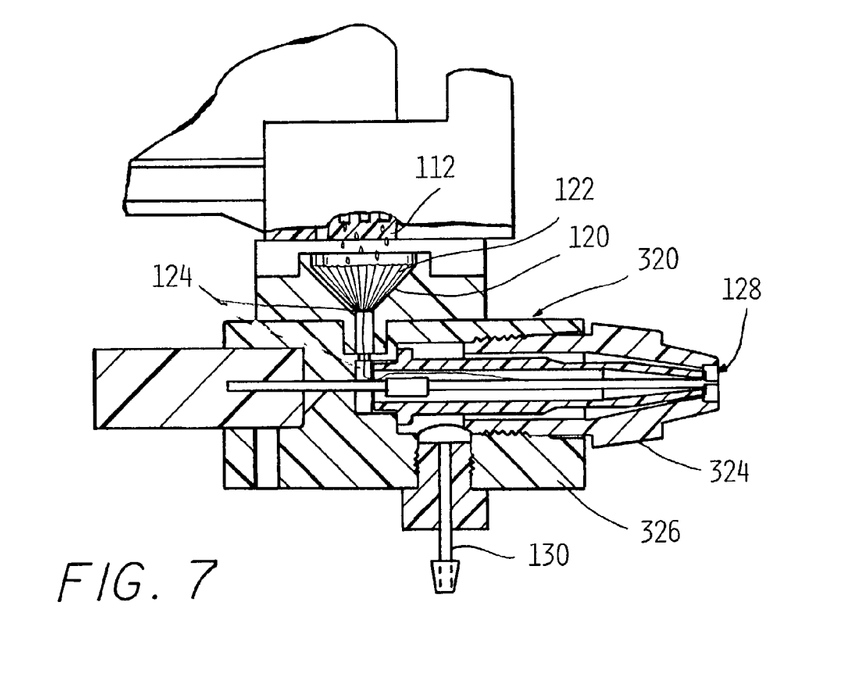
FIG. 7 is a partial cross section of a mixing surface device and atomization chamber of FIG. 6.
Figure 8:
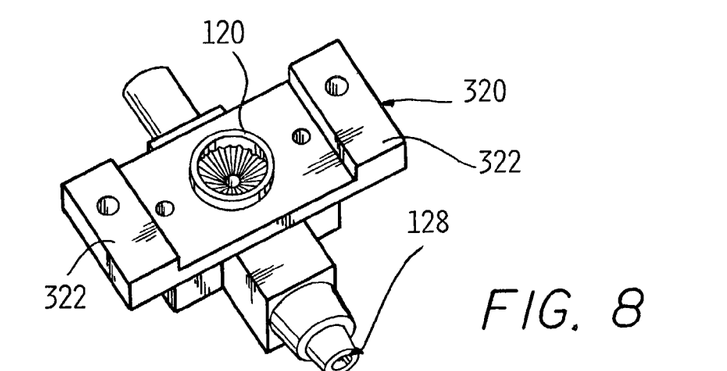
FIG. 8 is a top perspective view of a mixing surface suitable for use in the present invention.

Also disclosed is a mixing dispensing device 300 for use with a medical delivery system as depicted in FIGS. 6, 7, and 8. It is to be understood that the medical dispensing device 300 can be a stand-alone cartridge for integration into infusion pumps, dispensing systems, and the like. The medical dispensing device 300 includes a housing 310 with at least one reservoir located in the housing, which can contain at least one pharmaceutically active material as well as any other compatible materials desired or required. The mixing dispensing device 300 includes electronically controllable jetting devices such as device 112 associated with the housing 310 in fluid communication with the reservoir. The electronically controllable jetting devices dispense associate material associated therewith such as the pharmaceutically active material toward an end use destination. The device 300 can also include a suitable memory element such as data storage unit 140 previously discussed with regard to FIG. 3. The memory element 140 can be configured to interact with interface 142 to communicate with a source external to the mixing dispensing device 300. It is contemplated that communication can be to a suitable link in the medical delivery system which will permit the activation of appropriate jetting devices upon receipt of a suitable control command.

The mixing dispensing device 300 can be configured to include a mixing surface 120 permanently associated with housing 310. It is also contemplated that the mixing dispensing device can be composed of a housing 310 and a detachable mixing surface module 320 as shown in FIG. 7 in particular. The detachable mixing module 320 can include appropriate flanges 322 for positioning the mixing device 120 in appropriate position relative to electronically controllable jetting devices.

As depicted in FIGS. 6, 7 and 8, the mixing surface module 320, whether detachable or integral with the mixing dispensing device 300 as disclosed, can be configured to define and include mixing device 120 having mixing surface 122 in communication with orifice 124. The mixing surface module 320 can include or communicate with source of atomizing material 130 which can accomplish atomization at the region proximate to reference numeral 128. The atomized material can be directed or conveyed to the end use destination in any suitable manner or by any suitable mechanism. It is also contemplated that the device can be configured to convey a carrier stream past orifice 124 to facilitate introduction of the material from the mixing surface 122 into a suitable carrier stream as appropriate or desired. The carrier stream and mixed material can be atomized if desired or required.

It is to be understood that other devices and strategies for atomization can be included or employed in conjunction with the method and device as disclosed herein. Such suitable atomization techniques can include, but are not limited to, electrostatic, ultrasonic, air blast, air assist, rotary, and/or pressure atomization. The atomization technique employed will be one which can provide or produce atomized material of appropriate size, velocity and trajectory suitable for uptake and use in the organism or end use of intermediate application.

The carrier stream conduit 131 can have any suitable configuration for conveying materials upon exit from the exit orifice 124. It is contemplated that mixing can continue as the material are introduced into the carrier stream and conveyed to the end use destination. As depicted in FIG. 7, the device can include a separate exit nozzle 324 to direct the exiting stream as desired or required. The exit nozzle 324 as depicted in FIG. 7 is threadingly received in associated housing block 326.

The housing 310 can also be adapted to be associated with a suitable fluid mixing surface. It is contemplated that the fluid mixing surface will be positionable a discrete spaced distance from exit orifices defined in the electronically controllable jetting device(s). In this way, material can be dispensed into a suitable fluid carrier for further mixing and conveyance.

While the invention has been described in connection with what is presently considered to be the most practical and preferred embodiment, it is to be understood that the invention is not to be limited to the disclosed embodiment(s) but, on the contrary, is intended to cover various modifications and equivalent arrangements included within the spirit and scope of the appended claims, which scope is to be accorded the broader interpretation so as to encompass all such modifications and equivalent structures as is permitted under the law.

What is claimed:

1. A method for delivering a pharmaceutical composition, the method comprising:
   a) independently ejecting at least two liquids, wherein at least one of the liquids is pharmacologically active, the at least two liquids being ejected from an electronically controlled jetting device toward and directly onto a solid mixing surface; whereby, before being atomized, the at least two liquids become mixed while flowing on and channeling from the mixing surface out an exit orifice;
   b) conveying the mixed liquid to an atomizing device;
   c) atomizing the mixed liquid in the atomizing device; and
   d) directing the atomized liquid to an end use destination; wherein either:
   i) the solid mixing surface comprises at least one of a solid mesh material or a solid porous material, and the mixing medium comprises a combination of the solid mixing surface and a liquid material in communication with the solid mixing surface, or p1 ii) the solid mixing surface comprises a combination of a liquid material and a solid porous material acting as the solid mixing surface.

2. The method of claim 1, further comprising exerting a control limitation on the jetting device wherein the pharmacologically active liquid is ejected from the jetting device at a rate defined by the control limitation.

3. The method of claim 1 wherein a plurality of jetting devices are fluidically coupled with a plurality of storage receptacles, each storage receptacle configured to contain a liquid, wherein at least one liquid is pharmacologically active and at least one auxiliary liquid is compatible with the pharmacologically active material.

4. The method of claim 1, further comprising introducing a carrier stream proximate to the solid mixing surface, wherein the carrier stream includes a material compatible with the pharmacologically active liquid ejected from the jetting device.

5. The method of claim 1 wherein ejection of pharmacologically active liquid from the electronically controlled jetting device is governed by at least one conditional input selected from user health, current external environmental conditions, general activity level, metabolic condition, and combinations thereof.

6. The method of claim 1 wherein the solid mixing surface comprises a contoured surface configured to initiate mixing of pharmacologically active liquid ejected thereon.

7. The method of claim 6, further comprising exerting a control limitation on the electronically controllable jetting device, wherein the pharmacologically active liquid is ejected from the electronically controllable jetting device at a rate defined by the control limitation.

8. The method of claim 6 wherein a plurality of the electronically controllable jetting devices are fluidically coupled with a plurality of storage receptacles, each storage receptacle configured to contain a liquid, wherein at least one liquid is pharmacologically active and at least one additional liquid is compatible with the pharmacologically active liquid.

9. The method of claim 1 wherein at least one additional liquid is independently ejected from the electronically controlled jetting device and is a liquid compatible with the pharmacologically active liquid ejected from the electronically controllable jetting device.

10. The method of claim 9, further comprising exerting a control limitation on the electronically controllable jetting device, wherein the pharmacologically active liquid is ejected from the electronically controllable jetting device at a rate defined by the control limitation.

11. The method of claim 10 wherein a plurality of the electronically controllable jetting devices are fluidically coupled with a plurality of storage receptacles, each storage receptacle configured to contain a liquid, wherein at least one liquid is pharmacologically active and at least one auxiliary liquid is compatible with the pharmacologically active liquid.

12. A method for delivering a pharmaceutical composition, the method comprising:
a) independently ejecting proportionate quantities of liquid materials from associated electronically controllable jetting devices toward and directly onto a solid mixing surface, at least one liquid material exhibiting pharmacological activity; whereby, before being atomized, the ejected liquid materials become mixed while flowing on the solid mixing surface and channeling from the solid mixing surface out of an exit orifice;
b) atomizing the mixed liquid materials in an atomizing device; and
c) directing the atomized liquid materials to an end use destination;
wherein either:
i) the solid mixing surface comprises at least one of a solid mesh material or a solid porous material, and the mixing medium comprises a combination of the solid mixing surface and a liquid material in communication with the solid mixing surface, or
ii) the solid mixing surface comprises a combination of a liquid material and a solid porous material acting as the solid mixing surface.

13. The method of claim 12 wherein at least one liquid material ejected is an auxiliary liquid material, the auxiliary liquid material compatible with the liquid material having pharmacological activity.

14. The method of claim 13 wherein the proportionate quantities of liquid materials are ejected at programmably variable rates, the programmably variable rates determined by at least one conditional input electronically receivable by the electronically controllable jetting device.

15. The method of claim 14 wherein the conditional input is selected from user health, current external environmental conditions, general activity level, metabolic condition, and combinations thereof.

16. The method of claim 12, further comprising introducing a carrier stream into a region in communication with the exit orifice associated with the mixing surface to facilitate directing the flow of liquid materials to the end-use destination, wherein the carrier stream includes material compatible with the pharmacologically active liquid material ejected from an associated electronically controllable jetting device.

17. The method of claim 16 wherein the carrier stream is composed of a gas.

18. The method of claim 12 wherein the liquid materials are present in measured volumes, the measured volumes being ejected from associated electronically controllable jetting device in measured amounts over time.

19. The method of claim 12 wherein the liquid materials are ejected from associated electronically controllable jetting devices in measured amounts.

20. A device for delivering a pharmaceutical composition, the device comprising:

an electronically controllable jetting device in communication with at least two sources of liquids, at least one of the liquids being a pharmacologically active material;

an atomizing device; and a solid mixing surface having an exit orifice, the solid mixing surface positioned to directly receive the liquids from the at least two sources, the liquids being independently ejected from the electronically controllable jetting device, and the solid mixing surface configured such that the at least two liquids become mixed, before being atomized, while flowing on the solid mixing surface and channeling from the solid mixing surface to the exit orifice, the exit orifice configured to convey the pharmacologically active material away from the solid mixing surface and to the atomizing device;

wherein the solid mixing surface comprises a porous solid in fluid communication with a liquid material.

21. The pharmaceutical composition delivery device of claim 20, further comprising a chronometric device in electronic communication with the jetting device, the chronometric device capable of controlling ejection of pharmacologically active material based upon at least one of elapsed time and real time.

22. The pharmaceutical composition delivery device of claim 20, further comprising a data recording mechanism capable of receiving and maintaining data pertaining to at least one of dose quantity, dose frequency, administration rate, or type of material administered.

23. The pharmaceutical delivery device of claim 20, further comprising a carrier stream supply source, the carrier stream supply source configured to supply a carrier stream at a rate sufficient to disperse the pharmacologically active material introduced onto the mixing surface.

24. The pharmaceutical composition delivery device of claim 23 wherein the pharmacologically active material is conveyed into the carrier stream subsequent to exit from the solid mixing surface.

25. The pharmaceutical composition delivery device of claim 24, further comprising control electronics associated with the electronically controllable jetting device, the control electronics generating a command operable on the electronically controllable jetting device.

26. The pharmaceutical composition delivery device of claim 25 wherein the control electronics further comprise a chronometric device in electronic communication with the electronically controllable jetting device, the chronometric device capable of controlling ejection of liquid material based on at least one of elapsed time and real time.

27. The pharmaceutical composition delivery device of claim 26 wherein the control electronics are configured to act upon the electronically controllable jetting device to eject liquid on a programmed intermittent interval.

28. The pharmaceutical composition delivery device of claim 25, further comprising a user interface in electronic communication with the control electronics, the user interface capable of receiving data regarding at least one control parameter.

29. The pharmaceutical composition delivery device of claim 28 wherein the at least one control parameter includes at least one of user activation, biofeedback activation, or situational activation.

30. The pharmaceutical composition delivery device of claim 25, further comprising a conditional input interface in electronic communication with the control electronics, the conditional input interface configured to receive and process at least one input relevant in generating a command operable on the electronically controllable jetting device.

31. The pharmaceutical composition delivery device of claim 30 wherein the at least one input is selected from user health, external environmental conditions, physical activity level, metabolic condition, and combinations thereof.

32. A mixing dispensing device for use with a medical delivery system, the mixing dispensing device comprising:
    a housing;
    at least two reservoirs located in the housing, one of the reservoirs containing a pharmacologically active material and at least one other of the reservoirs containing an other material;
    an electronically controllable jetting device associated with the housing and in fluid communication with the at least two reservoirs, the electronically controllable jetting device independently ejecting the pharmacologically active material and the other material toward an end-use destination;
    a solid mixing surface interposed between the jetting device and the end-use destination, the solid mixing surface including a solid contact surface having an exit orifice, the solid contact surface positioned to directly receive the ejected pharmacologically active material and the other ejected material from the electronically controllable jetting device, whereby, before being atomized, the ejected materials become mixed while flowing on the solid contact surface and channeling from the solid contact surface out the exit orifice toward an atomizing device, the exit orifice being positioned to receive a flow of the ejected liquid from the solid contact surface and to direct the flow of the ejected liquid to the atomizing device;
    the atomizing device for atomizing the ejected fluid, the atomizing device positioned to direct a flow of atomized liquid to the end-use destination; and
    a memory element associated with the electronically controllable jetting device, the memory element configured to interactively communicate with a source external to the mixing dispensing device;
    wherein the solid mixing surface comprises a liquid in communication with the solid contact surface, and the solid contact surface comprises a porous material.

33. The mixing dispensing device of claim 32 wherein the solid contact surface of the solid mixing surface is contoured to initiate mixing of material ejected by the electronically controllable jetting device.

34. The mixing dispensing device of claim 32, further comprising control electronics associated with the jetting device, the control electronics configured to act on the jetting device to dispense the pharmacologically active material pursuant to a control limitation.

35. The mixing dispensing device of claim 32 wherein a plurality of the electronically controllable jetting devices are fluidically coupled with a plurality of storage reservoirs, each storage reservoir configured to contain a fluid, wherein at least one liquid is a pharmacologically active material and at least one additional liquid is compatible with the pharmacologically active material.

36. The mixing dispensing device of claim 32, further comprising a source of a carrier stream positioned proximate to the electronically controllable jetting device to receive pharmaceutically active material ejected therefrom.

37. The mixing dispensing device of claim 36 wherein the carrier stream includes a gaseous material compatible with the pharmaceutically active material ejected from the jetting device.

38. The mixing dispensing device of claim 32 wherein the electronically controllable jetting device is governed by at least one conditional input.

39. The mixing dispensing device of claim 38 wherein the conditional input is selected from user health, external environmental conditions, general activity level, metabolic condition, and combinations thereof.

40. The mixing dispensing device of claim 32, wherein the solid contact surface includes a contour portion, the solid contact surface configured to convey pharmacologically active liquid ejected thereon to an associated atomizing nozzle.

41. A cartridge for use with a medical dispensing system comprising;
    an electronically controllable jetting device in communication with at least two liquids, one of the at least two liquids being a pharmacologically active material;
    a mixing surface having an exit orifice, the mixing surface positioned to receive the at least two liquids independently ejected from the electronically controllable jetting device and wherein the mixing surface comprises at least one of a solid contact surface or a combination of a porous solid contact surface and a liquid material, whereby, before being atomized, the at least two liquids become mixed while flowing on the mixing surface and channeling from the mixing surface out an exit orifice opening toward a carrier stream source;

the carrier stream source configured to supply a carrier stream toward an atomizing device, the carrier stream being adjacent the exit orifice of the mixing surface; and the atomizing device for atomizing the material, the atomizing device positioned to direct the flow of atomized material toward an end-use destination;

wherein the exit orifice is configured to convey the pharmacologically active material away from the mixing surface into the carrier stream; and wherein the mixing surface comprises a detachable mixing surface module detachably mounted relative to the electronically controlled jetting device.

42. The cartridge of claim 41, further comprising a reservoir in fluid communication with the jetting device, the reservoir containing the pharmacologically active material and a material which is compatible with the pharmacologically active material, wherein each material is ejected through an associated electronically controllable jetting device.

43. The cartridge of claim 41, further comprising at least one memory device in electronic communication with the electronically controllable jetting device, the memory device containing at least one logic sequence governing the actuation of the jetting device.

44. The cartridge of claim 43 wherein the at least one memory device includes data relevant to material contained in the storage chamber.

45. The cartridge of claim 43 wherein the electronically controllable jetting device includes:
at least one electronically controlled nozzle member in fluid communication with a reservoir containing the pharmacologically active material; and
at least one control mechanism associated with the nozzle member, the control mechanism governing ejection of a measured quantity of the pharmacologically active material.

46. The cartridge of claim 45 wherein the control mechanism includes a data storage and control device, the data storage and control device containing at least one control sequence capable of generating at least one operational command actionable on the nozzle member.

47. The device of claim 28 wherein the control parameter includes at least one of user activation, biofeedback activation, or situational activation.

48. The method of claim 6 wherein the contoured surface comprises a combination of ridges and troughs.

49. The method of claim 12 wherein ejecting proportionate quantities of liquid materials comprises retaining, on the solid contoured mixing surface, the ejected fluids for a sufficient period of time to cause mixing of the ejected liquid materials.

* * * * *

UNITED STATES PATENT AND TRADEMARK OFFICE
CERTIFICATE OF CORRECTION

PATENT NO. : 7,563,244 B2
APPLICATION NO. : 10/285827
DATED : July 21, 2009
INVENTOR(S) : Blair M Kent et al.

It is certified that error appears in the above-identified patent and that said Letters Patent is hereby corrected as shown below:

In column 12, line 50, in Claim 1, after "or" delete "p1".

In column 16, line 20, in Claim 36, delete "pharmaceutically" and insert -- the pharmacologically --, therefor.

In column 16, line 23, in Claim 37, delete "pharmaceutically" and insert -- pharmacologically --, therefor.

In column 16, line 28, in Claim 39, after "wherein the" insert -- at least one --.

In column 17, lines 1-2, in Claim 42, after "active" delete "material, wherein each material is ejected through an associated electronically controllable jetting device." and insert -- material. --, therefor.

In column 17, lines 9-10, in Claim 44, after "relevant to" delete "material contained in the storage chamber." and insert -- at least one of the at least two liquids. --, therefor.

In column 18, line 6, in Claim 47, after "The" insert -- pharmaceutical composition delivery --.

In column 18, line 6, in Claim 47, after "wherein the" insert -- at least one --.

Signed and Sealed this

Sixteenth Day of March, 2010

David J. Kappos
*Director of the United States Patent and Trademark Office*